United States Patent [19]

Rodot

[11] 4,377,087

[45] Mar. 22, 1983

[54] DEVICE FOR ACOUSTICALLY CONTROLLING THE SETTING AND HARDENING CHARACTERISTICS OF CEMENTS

[75] Inventor: Francois Rodot, Pau, France

[73] Assignee: Societe Nationale Elf Aquitaine (Production), France

[21] Appl. No.: 199,283

[22] Filed: Oct. 21, 1980

[30] Foreign Application Priority Data

Oct. 11, 1979 [FR] France .............................. 79 25327
Sep. 29, 1980 [FR] France .............................. 80 20813

[51] Int. Cl.³ .......................................... G01N 29/00
[52] U.S. Cl. ..................................... 73/594; 73/597; 73/599
[58] Field of Search .................. 73/594, 597, 599, 618

[56] References Cited

U.S. PATENT DOCUMENTS

| | | | |
|---|---|---|---|
| 2,833,142 | 5/1958 | Runquist et al. | 73/597 |
| 3,316,755 | 5/1967 | Ensley | 73/597 |
| 3,537,541 | 11/1970 | Desai et al. | 73/597 |
| 4,259,868 | 4/1981 | Rao et al. | 73/597 |

FOREIGN PATENT DOCUMENTS

| | | |
|---|---|---|
| 2152805 | 4/1973 | Fed. Rep. of Germany . |
| 1294326 | 4/1962 | France . |
| 602852 | 4/1978 | U.S.S.R. . |

*Primary Examiner*—Stephen A. Kreitman
*Attorney, Agent, or Firm*—Poms, Smith, Lande & Rose

[57] ABSTRACT

The invention relates to a device for acoustically controlling the setting and hardening characteristics of a material such as cement. This device comprises a cell body defining a cylindrical body, or measuring chamber, which contains a receptacle adapted to receive the material to be tested. The measuring chamber is extended by its two ends by two cylindrical passages coaxial to said chamber, which comprise each a threaded portion and are associated to sealing means; said cell body further includes two electro-acoustic transducers which are arranged at mutually opposed locations and are facing each other. The novel device is adapted to be used for determining and controlling the setting, hardening and mechanical strength characteristics of cement or similar material under conditions of high pressure and elevated temperatures.

4 Claims, 7 Drawing Figures

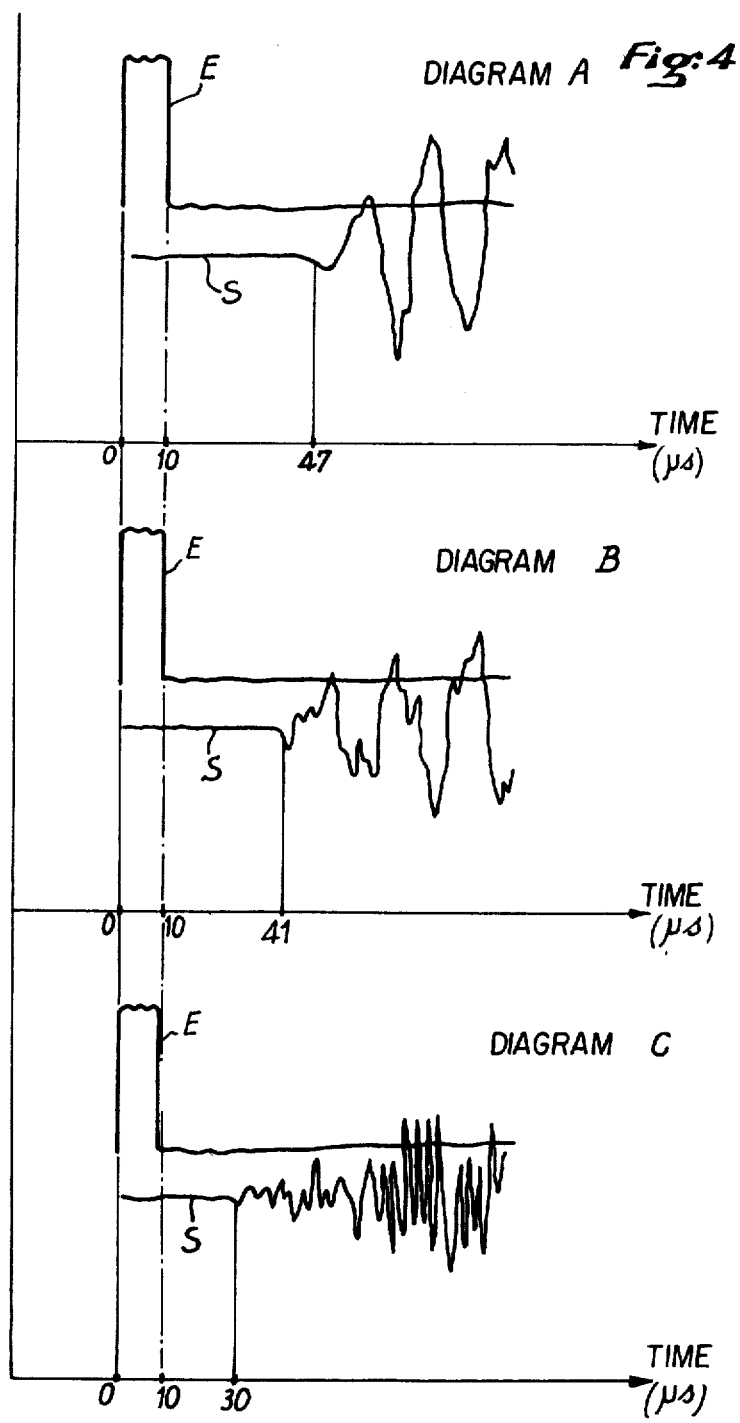

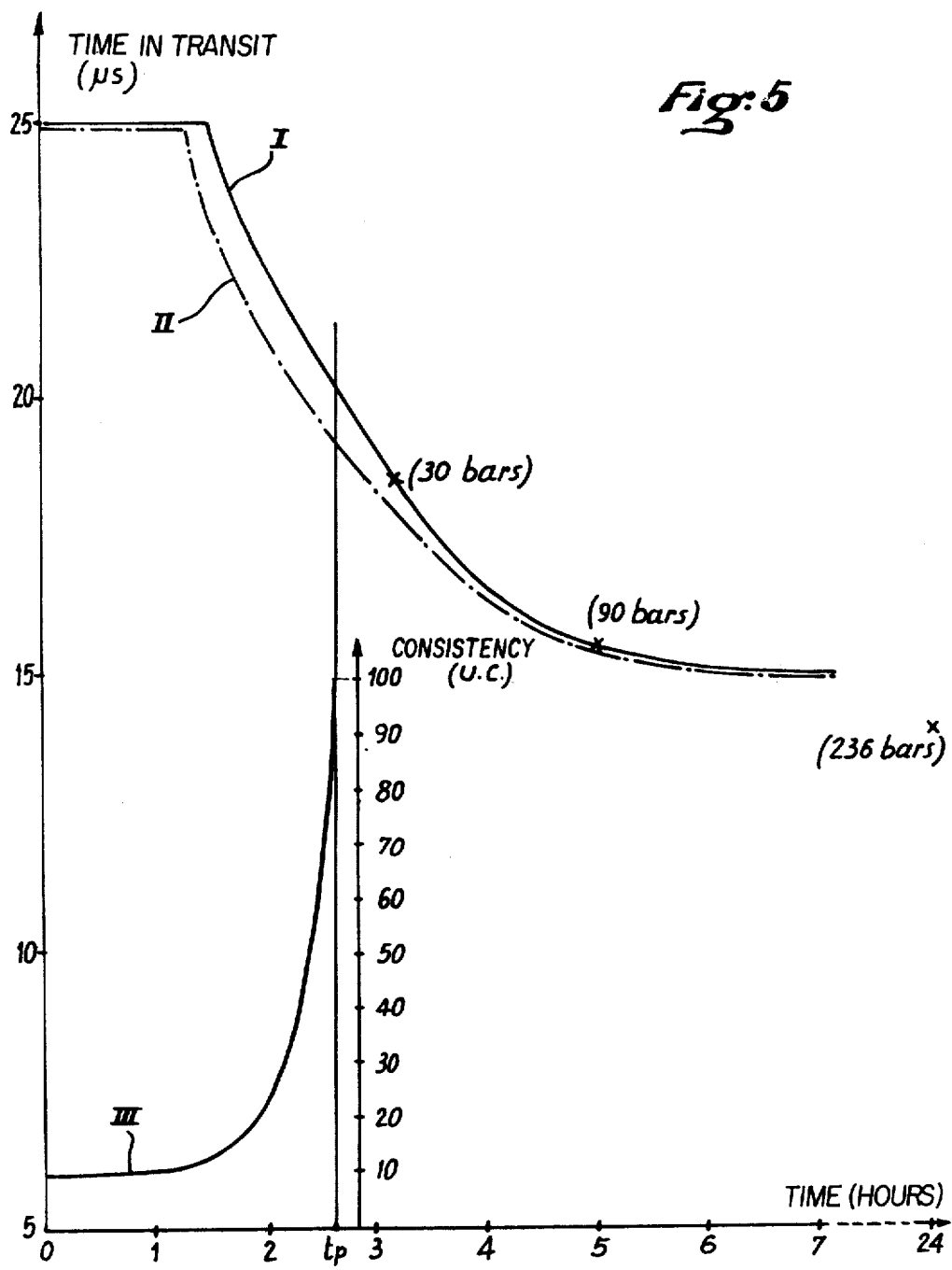

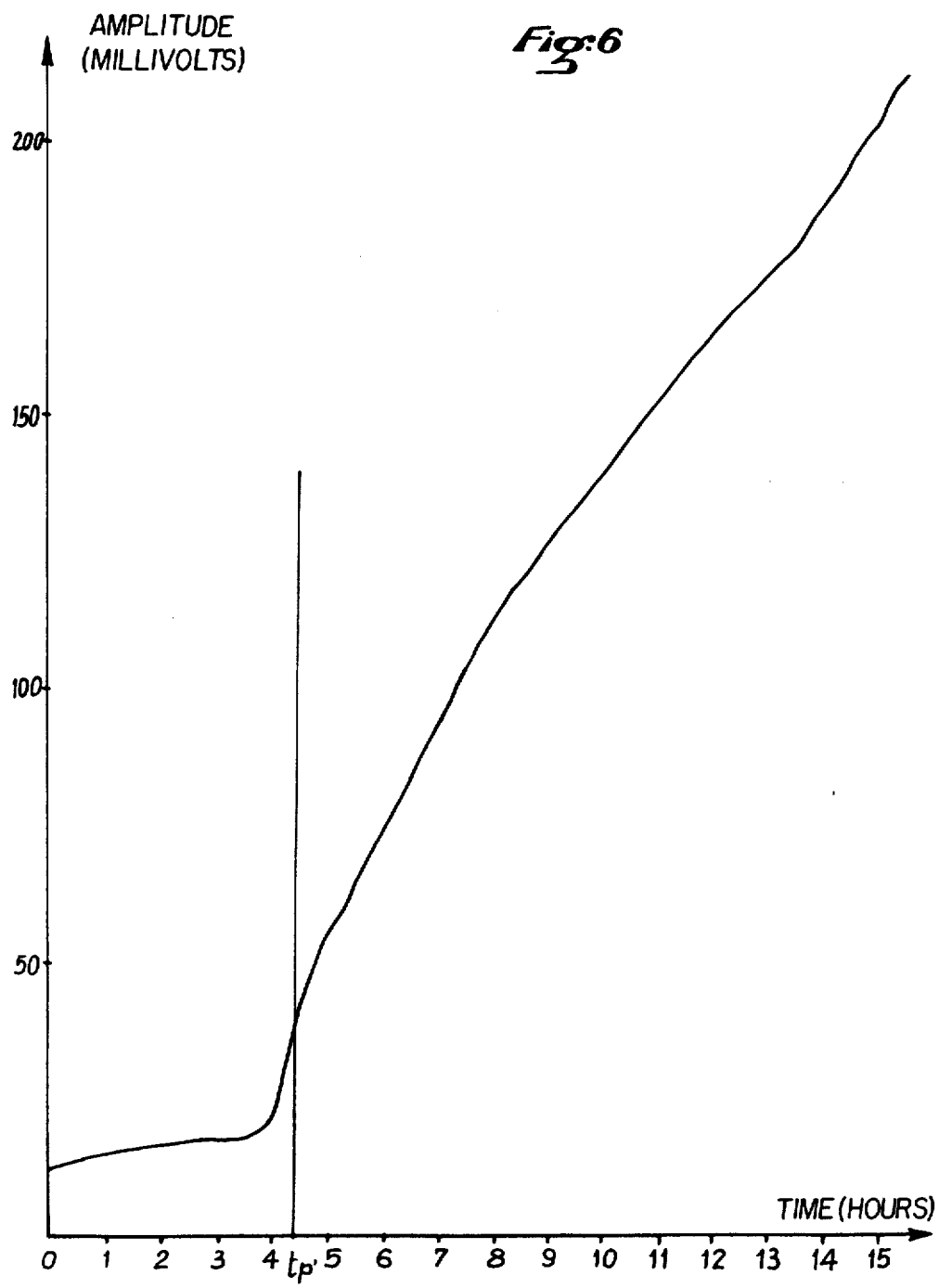

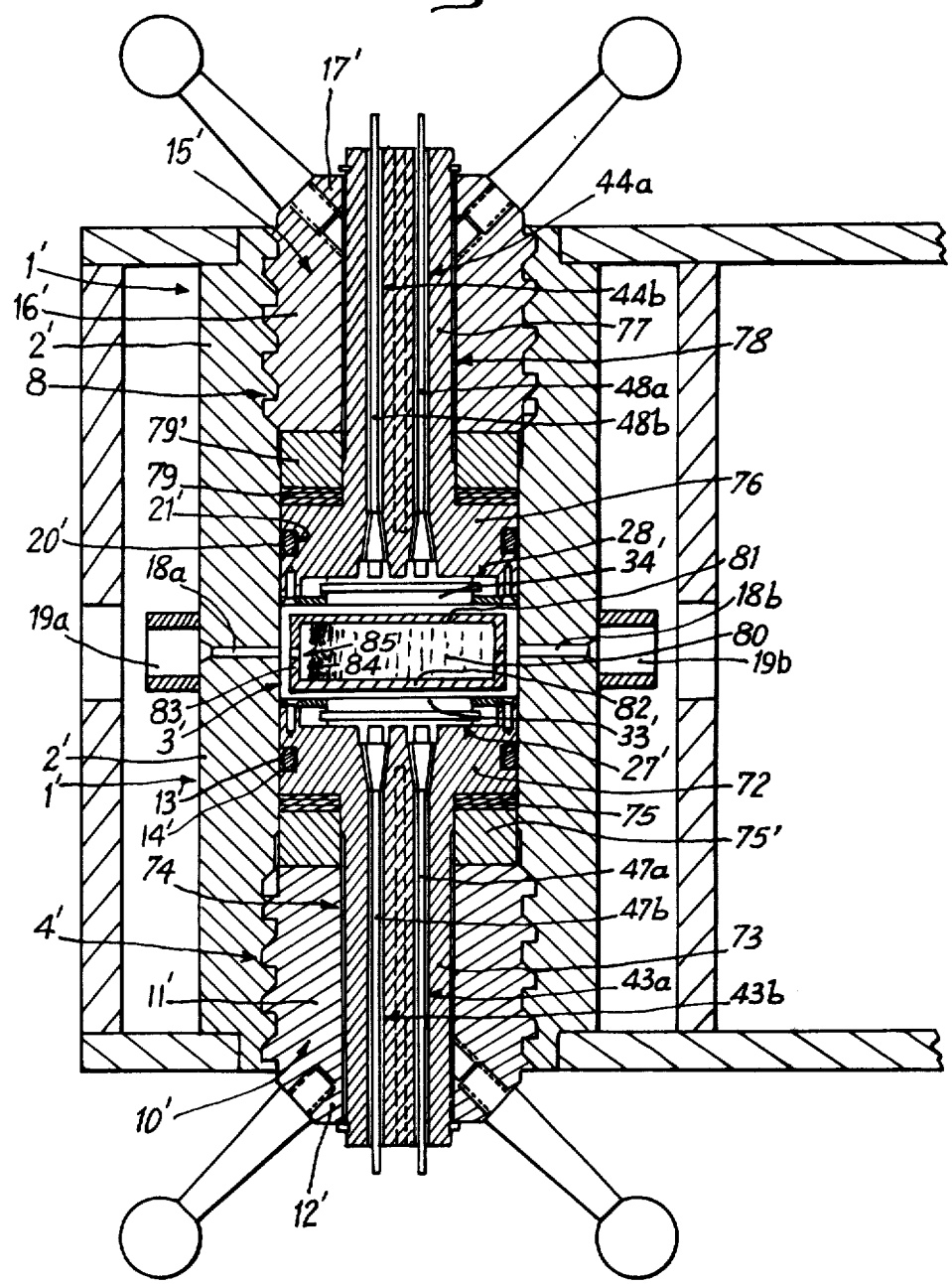

DEVICE FOR ACOUSTICALLY CONTROLLING THE SETTING AND HARDENING CHARACTERISTICS OF CEMENTS

The present invention is related to a cell for acoustically controlling the characteristics, especially the setting and hardening characteristics, of a material which passes from the liquid or paste-like state to the solid state, such as cement. More particularly, the invention concerns a cell for acoustically determining the pumpability time and the mechanical strength of cement. The invention is also related to apparatus including such cell for acoustically controlling the characteristics of materials of the above-mentioned kind.

During drilling operations it is often required to inject cement, especially for fixing the drilling tube columns to the drilling wall, or for separating the porous layers which may contain hydrocarbons. Under these conditions it is necessary to allow a certain period of time to elapse after each cement injection, so that the cement can set and acquire sufficient strength for allowing the subsequent operations to be carried out.

With a view to operating under optimum conditions the user is particularly interested in two characteristics of the cement used, to wit, the pumpability time (i.e. the period of time during which the mixed cement has a sufficiently low viscosity so that it can be pumped and thus injected into the drilling zone), and the so-called "waiting time" (i.e. the time which must be allowed to elapse for the cement to acquire a sufficiently high mechanical strength so that the drilling operations can be resumed). These two characteristics must be known, as accurately as possible, under the actual pressure and temperature conditions prevailing in the drilling zone wherein the cement is required to fulfill its desired functions.

Various devices for determining the pumpability time of cement are already known. One device generally used for laboratory measurements has been standardized by the American Petroleum Institute; this device allows the pumpability time of mixed cement to be measured under the actual pressure and temperature conditions to which said cement will be subjected during the pumping operations with a view to being injected into the zone to be cemented. This known device is based on the principle of measuring the moment or torque applied to a fixed blade by the mixed cement contained in a rotating bowl. When the torque reaches a predetermined value the cement has a viscosity defining the limit of pumpability. The technical specification which prescribes the use of this device—called "consistometer"—defines the pumpability time more particularly as being equal to the period of time after which the viscosity of the mixed cement reaches a value corresponding to 100 consistency units. This known device is bulky and expensive and furthermore it has to be serviced by trained specialists; consequently, it can only be used in a laboratory.

A known device for measuring the pumpability time which is adapted to be used in the field operates in accordance with a similar principle; however, the performances of this device are limited, since it can only be used under atmospheric pressure conditions and at temperatures lower than 100° C.

Another device adapted to be used in the field is known, the operating principle of which is based on the measurement of energy consumed by a motor which rotatively drives a blade immersed on a fixed bowl containing the mixed cement to be controlled with a view to reaching a predetermined viscosity of said cement, which device can be used at temperatures up to 200° C., but only at pressures not exceeding 35 bars.

Consequently, none of these two devices adapted to be used in the field can be used for determining the pumpability time under conditions of elevated pressure and temperature such as those prevailing when drilling operations are performed at a considerable depth.

The mechanical strength of cement, the variations of which allow the above-mentioned "waiting time" to be defined, is determined by a standard method of measuring the compression strength of the cement (ASTM-109-75-Specification). This method comprises determining the pressure required for crushing on a hydraulic press cement cubes which have previously been stored under the pressure and temperature conditions to be taken into consideration. For determining the mechanical strength corresponding to a predetermined instant, at least three cement cubes (50 mm width, length and depth) have to be crushed with a view to providing an average value. The equipment necessary for carrying out this testing method, including a hydraulic press, a cell for storing the cubic samples and moulds for forming the same, is considerable and cannot be used in the field (in situ). Furthermore, even when carried out in a laboratory this method is disadvantageous in that it constitutes a destructive test for which a great number of cubic samples must be prepared and used with a view to establishing the curve representing the mechanical strength of the cement as a function of time.

Thermometrical devices lowered into the drilling sites allow the setting process of the cement to be surveyed by measuring the amount of heat set free during said setting; however, the results obtained by this measuring method do not provide any indication regarding the mechanical strength of the cement.

Another device measures the setting phenomena of cement, resins and similar materials by acoustic means, i.e. by transmitting ultrasonic waves through the material during the setting thereof, and by determining the time of passage of said waves through the material (c.f. USSR patent No. 602 852). However, this equipment comprises a measuring cell which is not adapted to operate under the severe pressure and temperature conditions prevailing during drilling operations in great depth.

It is a primary object of the present invention to provide a cell for acoustically controlling the characteristics—especially the setting and hardening characteristics—of a material passing from the liquid or paste-like state to the solid state, such as cement, said cell having a simple, inexpensive structure and being adapted to be serviced easily, while being capable of operating under elevated pressure and temperature conditions in a laboratory as well as in the field. More especially, said cell is adapted to determine easily the pumpability time of cement and to provide, at the same time, continuously and without sample destruction, indications related to the mechanical strength of the cement under representative conditions.

The cell according to the invention comprises a cell body defining a cavity which forms a measuring chamber and which opens into the outer surface of said cell body through at least one passage adapted to contain a removable sealing plug, said measuring chamber including two electro-acoustic transducers having planar, mutually opposed emitting and receiving surfaces, said cell body being constituted by a hollow cylinder delimiting, by a cylindrical wall, a cavity comprising a median portion which constitutes said measuring chamber, and two end portions constituting two opposed passages adapted each to receive a removable sealing plug.

In the present disclosure and the appended claims, the term "electro-acoustic transducer" designates a device adapted to convert an electrical signal into acoustic waves, or to convert an acoustic wave into an electrical signal.

In one particular embodiment of the invention said two electro-acoustic transducers are located in two recesses provided in the cylindrical walls of the measuring chamber.

In this embodiment the cylindrical inner wall of the measuring chamber is provided near one of its ends with a bearing surface on which rests tightly a marginal portion of an elastic membrane separating a main portion of said measuring chamber, which includes two transducers, free from a secondary measuring chamber portion having a comparatively small volume and connected by a conduit to hydraulic fluid injection means, and to means for controlling the pressure of said fluid.

In a preferred embodiment said two transducers are located in recesses provided in the respective inner walls of said two plugs.

In this particular embodiment the measuring chamber includes a cylindrical receptacle provided with a sealable aperture allowing the material to be tested to be introduced into said receptacle, which latter furthermore comprises a channel located in the upper portion of the receptacle for equalizing the pressures prevailing respectively inside and outside the receptacle, said measuring chamber being connected by at least one channel provided in the wall of said cell to hydraulic fluid injection means and to pressure control means for measuring the pressure of said hydraulic fluid.

The cell according to the invention may also comprise temperature controlling means for adjusting the temperature of said cell to a predetermined value and for regulating this temperature with reference to said predetermined value, said temperature controlling means being constituted, for example, by heating rings or heating rods controlled by a thermocouple.

Preferably the transducers incorporated in the cell—which may advantageously be piezoelectric transducers—are associated with means for maintaining them under equal pressures in the recesses provided in the body of said cell.

The present invention is also related to apparatus comprising a cell of the above-defined type and used for determining by acoustic means the characteristics of a material which passes from the liquid or paste-like state to the solid state, such as—in particular—cement.

Such apparatus includes—very broadly speaking—in addition to the measuring cell an electric pulse generating system the output terminal of which is connected to the input terminal of the electro-acoustic transducer of the cell which acts as an emitter, and means for recording and/or displaying the electric output signal of the electro-acoustic transducer which functions as a receiver, and possibly for recording and/or displaying the electric signal transmitted to the emitting transducer, or for treating the said signal and recording and/or displaying a value representing their relative time shift and/or the ration of their respective amplitudes.

The present invention provides a device for measuring the travelling or transit time of the acoustic waves passing through a material during the process of setting and hardening, which time measurement can be used for determining e.g. the pumpability time and the mechanical strength of materials such as cement, as explained in more detail here-after, said device comprising, in addition to the measuring cell, an electric pulse generator feeding the emitting transducer of said cell and constituted by an electric control signal generator the output terminal of which is connected through a switch actuated by an initiator to the input terminal of the transducer, a time metering system, such as a quartz clock circuit receiving through a first input terminal the signal issuing from the switch and through a second input terminal the output signal of the receiving transducer of the cell, said system being actuated at the moment of beginning of the arrival of the electric pulse at the emitting transducer and being stopped when the output signal of the receiving transducer reaches a predetermined value, and means for recording and/or displaying the output signal of the time metering system, which signal represents the time of transit or travelling time of the acoustic waves through the material.

The invention also provides a device for measuring the attenuation of the amplitude of the acoustic waves travelling through the material, which attenuation allows, for example, the pumpability time to be determined when said material is cement, said device comprising in addition to the cell, an electric noise generator producing an electric noise of random frequency having a substantially constant amplitude and connected to the input terminal of the emitting transducer of the cell, as well as a recorder and/or a displaying (or visualizing) device receiving the output signal of the receiving transducer of the cell.

It is also possible to provide means for agitating the liquid or paste-like material while the same is setting within the measuring chamber, said agitating means being incorporated in said cell and being constituted, for example, by vibrating elements; alternatively, said elements may be mounted outside of said cell and be constituted by a support adapted, for example, to execute an alternating movement and onto which said cell is affixed, whereby said support transmits said movement to the entire cell assembly.

When controlling the pumpability time of cement which is to be pumped into a drilling site the mixed cement contained in the measuring chamber of the cell is agitated during a period of time corresponding to the duration of the pumping operation, with a view to effecting the control operation under representative testing conditions.

The invention will be described herein-below in more detail with reference to the appended drawings which are given by way of illustration, but not of limitation.

The description herein-below is related to an embodiment of the cell according to the present invention, and to two devices including such cell and which are adapted to be used for acoustically controlling the setting and hardening of material which passes from the liquid or paste-like state to the solid state, especially cement. In the appended drawings:

FIG. 4 is a diagram representing the recorded inlet and outlet signal at various stages of the setting process of the cement.

FIG. 5 is a comparative view of the two recordings obtained by the device according to FIG. 1, and recordings obtained by means of an API standard consistometer.

FIG. 6 is a diagram showing the amplitude of the output signal as a function of time, for a cement in the process of setting and subsequent hardening.

FIG. 7 is a cross-sectional view of a cell showing a different embodiment of the invention wherein the transducers are mounted within two plugs adapted to close opposite extremities of a measuring chamber.

Figure 1:
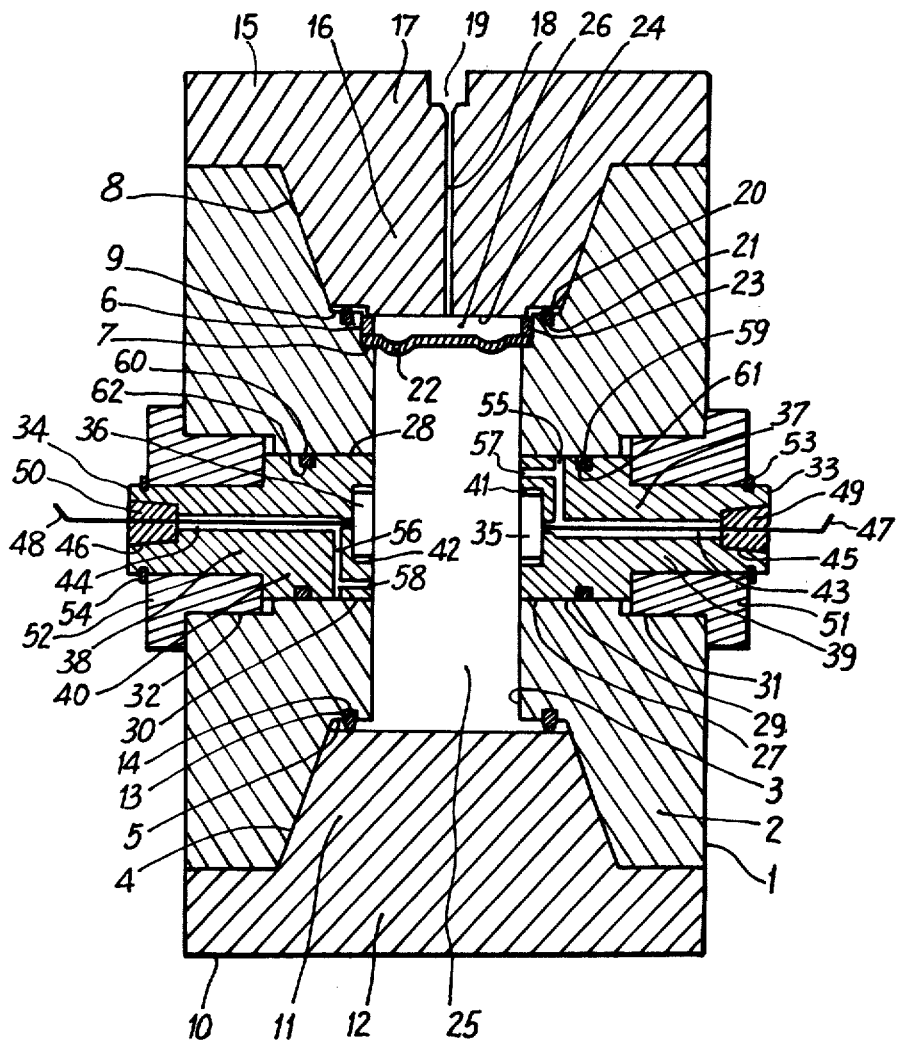
FIG. 1 shows a cross-sectional view of a cell wherein the transducers are mounted within two recesses provided in the walls of the measuring chamber.

As shown in FIG. 1, cell 1 comprises a cylindrical cell body 2 defining a cylindrical recess or cavity 3, or measuring chamber, which is coaxial to said cell body. At one of its ends said cavity is extended by a threaded frustoconical hollow portion 4 the axis of which coincides with that of the cavity 3, and the smaller diameter of which is greater than the diameter of cavity 3; said frustoconical hollow portion 4 flares outwardly and opens at the outside of the cell body. The lateral surface of said frustoconical portion 4 is connected to the lateral surface of cavity 3 by a bearing surface 5. The other end of the cavity 3 has a bore 6 coaxial to said cavity but having a diameter greater than that of the latter. The lateral surface of said bore is connected to the lateral surface of cavity 3 by a bearing surface 7. Bore 6 is extended by a threaded frustoconical hollow portion 8 coaxial to said bore and having a smaller diameter (or minimum diameter) greater than the diameter of cavity 3; said frustoconical portion 8 flares outwardly and opens at the outside of the cell body. The lateral surface of the bore is connected to the lateral surface of frustoconical portion 8 by a bearing surface 9. A first plug 10 comprising a threaded frustoconical body 11 provided with a cap 12 which forms a stop is screwed onto the corresponding threaded part of frustoconical portion 4 and thus seals the end of the cavity facing said plug. The tightness of this seal is obtained by a gasket 13 such as an O-ring mounted in a circular groove 14 provided in bearing surface 5. A second plug 15 having a frustoconical threaded body 16 provided with a cap 17 which forms a stop, and with a conduit 18 with a comparatively small cross-section, and extended by a high-pressure connecting piece 19 is screwed onto the corresponding threaded part of frustoconical portion 8 and thus seals the end of the cavity adjacent to the bore. The tightness of this seal is obtained by a gasket 20 such as an O-ring mounted in a circular groove 21 provided in bearing surface 9. Bearing surface 7 supports an elastic membrane 22 made of for example a metallic or elastomeric material and maintained in its position by a ring 23 on which bears a boss 24 having a diameter smaller than that of bore 6 and greater than the inner diameter of ring 23, which boss is provided at the end of plug 15. Said elastic membrane divides the space delimited by the lateral surface of the cavity and the inner ends of plugs 10 and 15 into two separate zones 25 and 26, one of which (i.e. zone 26) has a comparatively small volume.

The median part of the cell body defines two coaxial cylindrical recesses 27 and 28 located on either side of cavity 3 and the common axis of which meets the axis of said cavity. Each one of said recesses is constituted by a cylindrical bore and extended toward the outside of the cell body by a threaded cylindrical portion 31, 32 having a greater diameter and opening at the outer surface of said cell body. An electro-acoustic transducer assembly 33, 34 is mounted in each one of said recesses and constituted, for example, by a piezoelectric transducer maintained in a support 35, 36, by which said transducers are maintained under equal pressure, said transducer being located in the immediate vicinity of the cavity. Said support comprises a male portion 39, 40 and a female portion. Said male portion of each support comprises a cylindrical element slidably mounted in the bore of the corresponding recess, designated by numerals 27 and 28, respectively, and extended by a cylindrical element having a smaller diameter. Said male portion includes at its end directed toward the cavity, a space 41,42 respectively for the transducer, which space communicates with an axial conduit 43, 44 opening at the other end of said male portion through a threaded portion 45, 46 and serving i.a., to accomodate the electric conductor 47,48 respectively connected to the transducer. The tightness of the mounting of the conductor is obtained by a plug 49, 50 screwed onto the threaded portion of the conduit, said conductor being tightly mounted in said plug. The female portion 51,52 of each one of said supports is constituted by a ring member slidingly mounted on said smaller diameter element of the male portion of the support and maintained thereon by a retaining ring 43, 54, said ring member being screwed by means of an external threaded portion thereof onto the threaded part of the corresponding recess and comprising a cap having a comparatively large diameter which is adapted to engage the outer surface of the cell body.

The male portion of the support is provided with a radially extending conduit 55, 56 connecting the outer surface of said male portion to the axial conduit thereof; furthermore, said male portion is provided with a conduit 57, 58 connecting the radial conduit to its outer portion, adjacent to the recess. The tightness between the support and the corresponding recess is obtained by a gasket 59, 60 for example, an O-ring placed in a groove 61,62 provided in the lateral surface of the greater diameter cylindrical element of the male portion of said support.

In the diagram shown in FIG. 2, reference numeral 1 designates the cell described with reference to FIG. 1. The supply or input conductor of the electro-acoustic transducer- constituted for example by a piezoelectric transducer- incorporated in said cell and functioning as an emitter (in other words, for example, conductor 47 of transducer 35) is connected through a switch 64 actuated by an initiator 65 to the output of an electric control signal generator 63. The assembly constituted by generator 63, switch 64 and initiator 65 constitutes, for example, a generator of electric pulses of rectangular form. A time measuring system 66 constituted more particularly by a quartz clock circuit, receives through a first input terminal the electric signal issuing from switch 64 and through a second input terminal the output signal transmitted by a conductor 48 from electro-acoustic transducer (or piezoelectric transducer) 36 of cell 1, which acts as a receiver. Said time metering system is actuated, or triggered, at the beginning of the emission of the signal in the form of an electric rectangular pulse, and it is stopped when the output signal of transducer 36 transmitted through conductor 48 reaches a predetermined value or level. The time metering system produces a signal representing the transit time of the acoustic waves travelling through the material contained in the measuring chamber of cell 1. Said signal is transmitted to a recorder 67 where the curve representing the variations of the transit time as a function of time is recorded. A system designated generally by reference numeral 68, comprising a plurality of electric heating rings surrounding the body of cell 1 and controlled by a thermocouple provided within said cell body, allows the cell to be heated to a predetermined temperature, and allows said temperature to be regulated. When testing cement which is to be injected into a drill site, it is possible, in particular, to raise said temperature progressively, with a view to reproducing the conditions prevailing during the actual injection of said cement. When it is desired to operate under controlled temperature conditions, cell 1 is placed in a heatproof (i.e. thermically isolated) enclosure. A pneumatic system 69, such as a hydraulic pump, for amplifying and controlling the pressure is connected to the high pressure connecting piece 19 of cell 1 with a view to injecting a pressurized hydraulic fluid into chamber 26 of cell 1, so as to confer on the pressure acting on membrane 22 of said cell a desired value, and to regulate said pressure. When testing cement to be injected into a drilling site it is possible to create a progressively increasing pressure with a view to reproducing or simulating the conditions encountered by the cement during injection.

Figure 2:
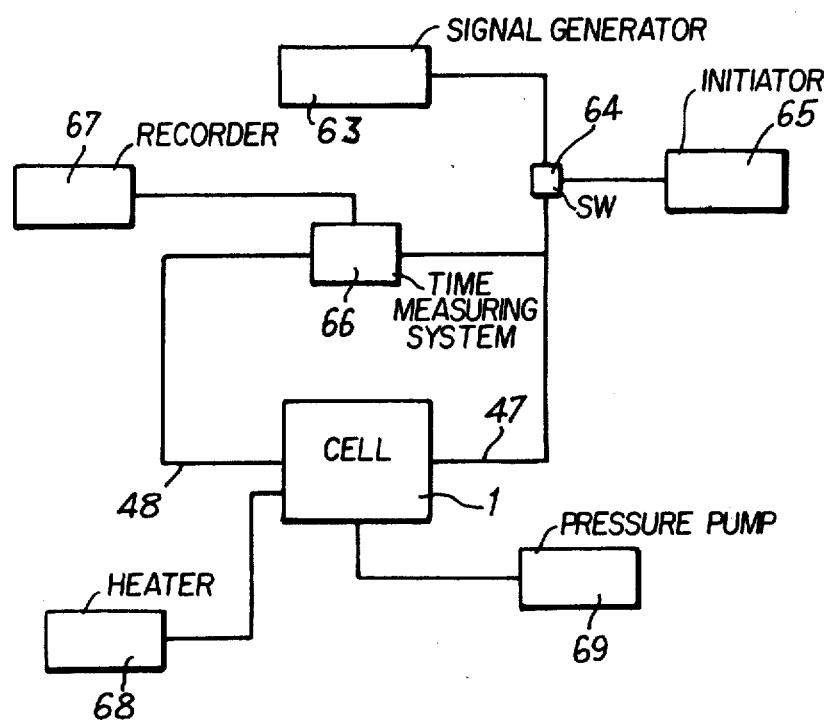
FIG. 2 is a diagrammatic view of the transit time metering or measuring device.
Figure 3:
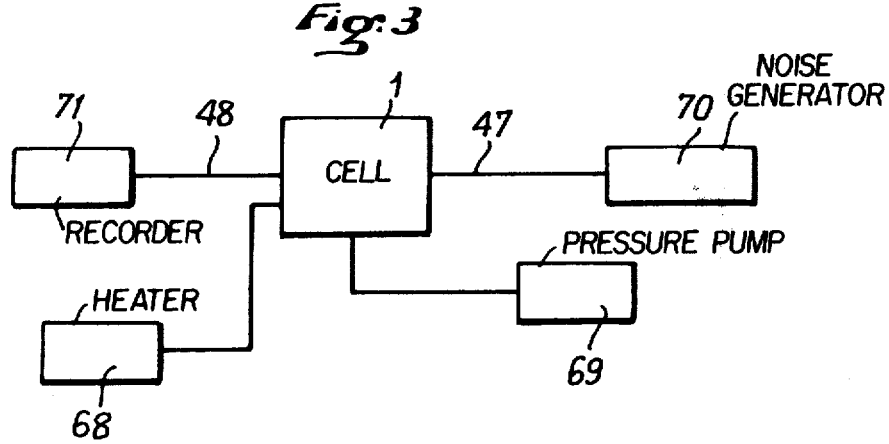
FIG. 3 is a diagrammatic view of a device for measuring the amplitude attenuation.

In the diagram of FIG. 3 reference numeral 1 designates a cell such as described with reference to FIG. 1. In this embodiment the device also comprises a supply or input conductor 47 associated to electro-acoustic (e.g. piezoelectric) transducer 35 functioning as an emitter, and a conductor 48 transmitting the signal issuing from electro-acoustic (e.g. piezoelectric) transducer 36 functioning as a receiver. Reference numerals 68 and 69 designate respectively the heating and temperature control system of cell 1 and pneumatic pressure amplification and control system of said cell, as described in detail with reference to FIG. 2. A random frequency electric noise generator 70 producing electric noise of a substantially constant amplitude feeds conductor 47 of transducer 35 which acts as an emitter. Conductor 48 of transducer 36 acting as a receiver is connected to the input of a recorder 71. Said recorder produces a diagram representing, as a function of time, the variations of the amplitude of the acoustic waves produced on the basis of the signal emitted by the noise generator and having travelled through the material to be tested. While the amplitude of the generator signal is substantially constant, the signal received by the recorder represents the attenuation of the acoustic waves which have travelled through the material. Due to the utilisation of a random frequency noise generator the attenuation of the signal resulting from resonance phenomena during the passage of the waves through the cell is eliminated.

The test procedure for surveying the setting and hardening of a material passing from the liquid or paste-like state to the solid state, especially the setting and hardening of cement, using the apparatus according to any one of FIGS. 2 and 3, including the cell described with reference to FIG. 1, may be explained schematically as follows. At first, cell 1 is opened by withdrawing plug 15, ring 23 and membrane 22, and the walls of measuring chamber 3 are lubricated with a view to avoiding any adherence of the material to be tested. Said material, e.g. cement mixed with water (when the material to be tested is cement) is introduced into the measuring chamber up to the level defined by bearing surface 7, whereafter the membrane is put in place, then the ring is placed onto the membrane and finally plug 15 is screwed in place. Furthermore, the conduits of each transducer supports are filled with oil in such a manner that the transducers are maintained under equal pressures. Cell 1 thus prepared and containing the material to be tested is placed into a heatproof enclosure, and cell heating and temperature regulating system 68, as well as pressure amplifying and regulating system 69 determining the pressure acting on membrane 22 are actuated. The output terminal of the electric pulse generating assembly comprising generator 63, switch 64 and initiator 65 (as shown in FIG. 2) or random frequency constant amplitude noise generator 3 (as shown in FIG. 3) is connected to conductor 47 associated to emitting transducer 35 of the cell, while output terminal 48 of transducer 36 of said cell is connected (as shown in FIG. 2) to one of the input terminals of time metering system 66, the other input terminal of which is connected to the output terminal of switch 64, the output of system 66 being connected to recorder 67; alternatively, (as shown in FIG. 3) output terminal 48 of transducer 36 is connected directly to recorder 71. When the pressure and temperature conditions of the cell correspond to the predetermined values the pulse or noise generator is actuated and the thus produced electric pulses energize the emitting transducer which produces acoustic waves travelling through the tested material toward the receiving transducer which latter converts the acoustic energy thus received into an electric signal. A signal is recorded as a function of time, which represents either the transit time of the acoustic wave travelling through the material being tested (in the case of the embodiment shown in FIG. 2) or the attenuation of the acoustic wave having passed through said material (in the case of the embodiment shown in FIG. 3). In the embodiment shown in FIG. 2 the pulsed generator emits rectangular electric pulses having a predetermined width (for example 10 microseconds) which are repeated at a frequency (for example according to a periodicity of 100 microseconds) such that the corresponding recording of one pulse is entirely terminated when the emission of the following pulse starts.

FIG. 4 shows, starting from an identical time origin, to wit: the instant zero of the starting of the emission of a rectangular pulse having a duration of 10 microseconds, the electric signal E representing said pulse which is transmitted to the emitting transducer and the resulting output signal S of the receiving transducer of the cell incorporated in the embodiment according to FIG. 2, in three different stages of the evolution of a cement (type CPA cement mixed with 46% fresh water, by weight of the cement); to wit, liquid cement, (diagram A) cement at the beginning of the setting process (diagram B) and hardened cement (diagram C). When comparing these diagrams it will be seen that the transit time of the acoustic waves through the tested material (i.e. the difference between the instant of the appearance of a signal of a predetermined level at the output terminal of the receiving transducer and the instant of the start of the emission of the rectangular initiating pulse of the emitting transducer) decreases substantially while the cement passes from the liquid state (diagram A showing a transit time of 47 microseconds) through the phase of initial setting (diagram B showing a transit time of 41 microseconds) to the final hardened state of the cement (diagram C showing a transit time of 30 microseconds). In other words, the velocity of the acoustic waves passing through the cement increases substantially while the cement passes from the liquid state to the setting phase and finally to the hardened state.

Curves I and II in FIG. 5 represent, as a function of time, the variations of the transit time in microseconds (for a class G cement mixed with 44% fresh water, by weight of cement, without any additive substance) said transit time being measured by means of the device shown in FIG. 2, using rectangular initiating pulses of a period of 100 microseconds having a width of 10 microseconds, the cell of the device comprising a measuring chamber having a diameter of 40 mm. Curve I has been obtained while operating under atmospheric pressure and at a temperature of 48° C., whereas curve II corresponds to an operation effected at 48° C. under a pressure of 200 bars, the pressure increase being completed within 30 minutes from the start of the emission. Furthermore, in the same Figure curve III represents, using the same time scale on the abscissa, the consistency curve obtained by a test of cement by means of a standard API consistometer. It can be seen that the start of the setting of the cement according to the standardized consistometer (the consistency value reaching 100 Consistency Units (C.U.)) corresponds to an abrupt change of the transit time (curves I and II). The pumpability time of the cement, the standardized definition of which corresponds to the time period at the end of which the consistency of the mixed cement reaches a value of 100 C.U. as measured by the standard consistometer, and corresponds to the abscissa $t_p$ on the diagram of FIG. 5 is the equivalent of 20% of the transit time.

The compression strength of the cement, as measured by means of a hydraulic press after 3.25 hours, 5 hours and 24 hours, was equal to 30 bars, 90 bars and 236 bars respectively. This increase with time of the compression strength of the cement (hardening of the cement) corresponds to a decreases of the transit time as listed herein-below:

| compression strength (bars) | 30 | 90 | 236 |
|---|---|---|---|
| decreases of transit time (%) | 22 | 36 | 42 |

Referring to a given type of cement, the measure of the decrease of the time of transit of the acoustic waves passing through the cement during setting and then during hardening allows, on the one hand, a value representing the pumpability time of the mixed cement, and on the other hand, the compression strength of the hardened cement to be determined, which latter indication allows the waiting time prior to resuming the drilling operations associated with cement injection to be determined.

The behaviour of the above-mentioned cement may be described summarily as follows, in relation to the decrease of the transit time as defined herein-before:

| Decrease of transit time (%) | State of evolution of the cement |
|---|---|
| 0 | Liquid cement |
| 0–10 | Thickening |
| 10–20 | Pumpability time |
| 22 | Strength: 30 bars |
| 36 | Strength: 90 bars |
| 42 | Strength: 236 bars |

When comparing curves I and II it will be seen that at a given instant of time during the time interval corresponding to the setting of the cement, the transit time is comparatively shorter while the pressure is comparatively higher, which indicates a comparatively advanced stage of evolution of the cement.

This clearly shows that it is necessary for the user to known the value of the pumpability time under the pressure and temperature conditions which will be actually encountered by the cement, especially when said cement is used under conditions of elevated pressure and temperature, with a view to avoiding the premature setting of the cement. This shows one of the important advantages of the cell according to the invention, for testing cement, even under conditions of elevated pressures and elevated temperatures.

The curve shown in FIG. 6 represents, as a function of time, the amplitude of the electric output signal of the receiving transducer of cell 1 incorporated in the device according to FIG. 3, with reference to a APC (Artifical Portland Cement) cement mixed with 46% fresh water, using a measuring chamber of 40 millimeters under conditions of temperature and pressure which correspond to ambiant temperature and atmospheric pressure. The amplitude of said signal, which is a function of the attenuation of the acoustic waves having passed through the tested cement (a low amplitude corresponding to a high attenuation of the said acoustive waves and vice versa) remains very low as long as the cement is in the liquid state, then increased abruptly at the instant of the beginning of the setting process, whereafter the amplitude continues to increase. The instant when the beginning of the evolution is recognized furthermore corresponds to the value $t'_p$ of the pumpability time as measured by means of the Standard API consistometer. The acoustic impedance of the medium then continues to decrease (decreasing attenuation) during the hardening of the cement.

When the variations, as a function of time; of the amplitude of the above-mentioned signal (which is a function of the attenuation of the amplitude of the acoustic waves passing through the setting and hardening cement) that are produced by a constant level initiating signal are known, it is possible furthermore to determine a value corresponding to the pumpability time of the cement, which value represents the duration at the end of which an abrupt increase of the amplitude of said recorded signal is observed.

Referring to FIG. 7, it will be seen that cell 1' as shown comprises a cylindrical cell body 2' defining a cylindrical cavity the median portion 3' of which constitutes the measuring chamber, and the end portions 4' and 8' of which are coaxial to portion 3' and constitute two opposite passages or conduits each of which is provided with a screw thread and adapted to receive a respective plug 10', 15', each one of said plugs being provided with a convenient screw thread.

Plug 10' is mounted in passage 4' and comprises a cylindrical body or piston 72 linearly displaceable in cylindrical cavity 3' and extended by a coaxial cylindrical rod 73 slidably mounted in a coaxial cylindrical passage or conduit 74 through an externally threaded nut 11'. Nut 11' is extended by an annular cap 12' provided with tightening levers or handles.

The tightness of the mounting of plug 10' is obtained, on the one hand, by an O-ring 13' placed into a circular groove 14' provided in the external surface of cylindrical body 72 and, on the other hand, by an annular Teflon gasket 75 placed into an annular space delimited by cylindrical body 72, nut 11' and the cylindrical wall of cavity 3'. Gasket 75 is separated from nut 11' by a supporting ring 75'.

Plug 15' similar to plug 10' is located in passage 8' and comprises a cylindrical body or piston 76 linearly displaceable in cylindrical cavity 3' and extended by a coaxial cylindrical rod 77 slideably mounted in a coaxial cylindrical passage or conduit 78 through an externally threaded nut 16'. Nut 16' is extended by an annular cap 17' provided with tightening levers or handles.

The tightness of the mounting of plug 15' is obtained, on the one hand, by an O-ring 20' placed in a circular groove 21' provided in the external surface of cylindrical body 75 and, on the other hand, by an annular gasket 79 made of Teflon located in an annular space delimited by cylindrical body 76, nut 16' and the cylindrical wall of cavity 3'. Gasket 79 is separated from nut 16' by a supporting ring 79.

A coaxial cylindrical recess 27' is provided in cylindrical body or piston 72 which is part of plug 10', and an electro-acoustic transducer assembly 33', constituted for example by a piezoelectric transducer, is placed in said recess 27' and mounted on a pressure equilibrating support; more particularly, transducer 33' is mounted in such a manner that it remains immersed in a pressure transmitting fluid. Said electro-acoustic transducer assembly 33' is connected to electric supply means (not shown) by supply cables 47a and 47b. Cables 47a and 47b are isolated and extend through coaxial cylindrical rod 73 which is provided for this purpose with two borings 43a and 43b including sealing means (not shown).

Similarly cylindrical body or piston 76, which is part of plug 15, comprises a coaxial recess 28' wherein an electro-acoustic transducer assembly 34', constituted for example by a piezoelectric transducer, is mounted and maintained by a pressure equilibrating support; more particularly, transducer is mounted in such a manner that it remains immersed in a pressure transmitting fluid. Electro-acoustic transducer assembly 34' is connected to electric supply means (not shown) by cables 48a and 48b. Cables 48a and 48b are isolated and extend through two borings 44a and 44b provided in each coaxial rod 77 and including sealing means (not shown).

One of said transducers, for example, transducer 33', is connected to the supply by emitting means, while the other transducer 34' is connected to the supply source by receiving and time metering means.

In the median zone of cylindrical cavity 3' the wall of cell body 2' is provided with a boring 18a having a small cross-section and extending toward the outside through a high pressure connecting piece 19a adapted to be connected to a pressurized hydraulic fluid supply conduit (not shown).

The wall of cell body 2' also comprises a boring 18b having a small cross-section and extending toward the outside through a high pressure in inlet 19b adapted to be connected to a pressure relief sump (not shown).

A cylindrical receptacle 80 is mounted within cylindrical cavity 3' delimited by the internal surfaces of plugs 10' and 15' (i.e. within the measuring chamber); said cylindrical receptacle is delimited by the walls 81 and 82 having a constant thickness and planar parallel surfaces. Receptacle 80 comprises a removable cover 83 which allows cement mortar to be introduced up to a certain level 84, said cover being provided with a boring 85 for equalizing the pressure by means of the hydraulic fluid between the interior and the outside of the said receptacle.

The device described with reference to FIG. 7 comprises the same basic elements as those used in the embodiment shown in FIG. 1, said elements being arranged in such a manner that assembling and disassembling the same is substantially facilitated.

The process of testing or controlling the setting and the hardening of cement, using the device according to any one of FIGS. 2 and 3, provided with the cell described with reference to FIG. 7 may be summarily described as follows.

Cell 1' is opened by removing plug 15'; cavity 3' then contains a film of pressurizing oil on its various walls. The cement mortar to be tested is then poured into receptacle 80 until it reaches the level indicated at 82, cover 83 is put back into place and blocked. Cell 1' being mounted on a support in such a manner that the axis of cavity 3' is substantially horizontal, receptacle 80 can be slideably inserted into said recess 3 while cover 83- and thus boring 85- are maintained in an upper position, thus eliminating any risk of spilling cement mortar.

Plug 15' is then put in place and blocked. The filling of the remaining spaces of cavity 3' with pressurizing oil is achieved by an appropriate oil circulation. The desired temperature and pressure conditions are then established in the cell and it is thus possible to start the control of the physical parameters of the cement.

It will be easily understood that since consequently cavity 3' is not polluted by the presence of cement it is very easy to pass from one control operation to the subsequent one.

The invention is not limited to the embodiments shown and disclosed herein-above; many modifications and variants can be envisaged by those skilled in the art within the spirit and scope of the invention as defined by the appended claims.

What is claimed is:

1. A cell for acoustically controlling the characteristics such as the setting and hardening characteristics of a material which passes from the liquid or paste-like state to the solid state, such as cement, comprising:
   a cell body defining a cavity which forms a measuring chamber and which opens into the outer surface of said cell body through at least one passage adapted to contain a removable sealing plug,
   said measuring chamber including two electro-acoustic transducers having planar, mutually opposed emitting and receiving surfaces,
   said cell body being constituted by a hollow cylinder delimiting, by a cylindrical wall, a cavity comprising a median portion which constitutes said measuring chamber, two end portions of said cavity constituting two opposed passages adapted each to receive a removable sealing plug,
   said cylindrical wall of said measuring chamber being provided with two recesses for reception of said two electro-acoustic transducers,
   said cylindrical inner wall of the measuring chamber being provided near one of its ends with a bearing surface on which rests tightly a marginal portion of an elastic membrane separating a major portion of said measuring chamber, which includes the two transducers, from a secondary measuring chamber portion having a comparatively small volume and connected by a conduit to a hydraulic fluid injection means and to means for controlling the pressure of said fluid.

2. A cell for acoustically controlling the characteristics such as the setting and hardening characteristics of a material which passes from the liquid or paste-like state to the solid state, such as cement, comprising:

a cell body defining an internal cavity which forms a chamber and which has communication with at least one passageway adapted to contain a removable sealing plug therefor, two electro-acoustic transducers having planar mutually opposed emitting and receiving surfaces arranged in said chamber;

a cylindrical receptacle for containing material to be tested adapted to be placed in said chamber when said sealing plug is removed, said cylindrical receptacle being provided with a sealable aperture for introducing material to be tested into said receptacle, said receptacle being provided with a port located in spaced relation to test material contained in the receptacle and in communication with said chamber, the interior of said chamber being in communication with hydraulic fluid injection means and pressure control means adapted to control the pressure of said fluid, said receptacle containing the material to be tested being immersed and supported in pressure fluid in said chamber, said pressure fluid within and without said receptacle being equalized.

3. A device for acoustically determining pumpability time and setting and hardening characteristics of a material adapted to pass from a flowable state to a nonflowable solid state under preselected pressures and temperatures, comprising in combination:

a body member having an internal chamber;

means on said body member providing access to said chamber to introduce material to be tested into said chamber;

two electro-acoustic transducers having spaced opposed emitting and receiving surfaces, respectively, in said chamber;

a receptacle containing material to be tested adapted to be placed in said internal chamber through said access means;

passageway means in said body member in communication with said internal chamber for introducing pressure fluid into said chamber around said receptacle;

said pressure fluid supporting said receptacle in said chamber;

means including a port in said receptacle in communication with said pressure fluid for equalizing pressure within and without said receptacle;

and means for imparting through said pressure fluid selected pressures to said material to be tested in said receptacle;

said pressure fluid providing equilibrating support to said transducers.

4. A device as stated in claim 3 including means for heating said material to a selected temperature simulating representative conditions to be encountered during use of the material.

* * * * *